(12) United States Patent
Sengun et al.

(10) Patent No.: US 8,425,517 B2
(45) Date of Patent: Apr. 23, 2013

(54) ABRASIVE CUTTING SYSTEM AND METHOD

(75) Inventors: Mehmet Z. Sengun, Farmingham, MA (US); Elizabeth Heneberry, Westwood, MA (US); Ian D. McRury, Medway, MA (US); Kevin J. Ranucci, Warwick, RI (US); Douglas W. Dunn, Mansfield, MA (US)

(73) Assignee: DePuy Mitek, Inc., Raynham, MA (US)

( * ) Notice: Subject to any disclaimer, the term of this patent is extended or adjusted under 35 U.S.C. 154(b) by 0 days.

(21) Appl. No.: 13/188,983

(22) Filed: Jul. 22, 2011

(65) Prior Publication Data
US 2012/0029519 A1    Feb. 2, 2012

Related U.S. Application Data

(62) Division of application No. 10/905,351, filed on Dec. 29, 2004, now abandoned.

(51) Int. Cl.
*A61B 17/00*    (2006.01)
(52) U.S. Cl.
USPC .......................................................... 606/79
(58) Field of Classification Search .......... 606/79; 451/30, 60, 446
See application file for complete search history.

(56) References Cited

U.S. PATENT DOCUMENTS

| | | |
|---|---|---|
| 3,930,505 A | 1/1976 | Wallach |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,380,138 A * | 4/1983 | Hofer .............................. 451/40 |
| 4,430,416 A | 2/1984 | Goto et al. |

(Continued)

FOREIGN PATENT DOCUMENTS

| | | |
|---|---|---|
| DE | 19804065 A1 | 12/1999 |
| DE | 19904640 A1 | 8/2000 |

(Continued)

OTHER PUBLICATIONS

Allcock, The Encyclopedia of Polymer Science, vol. 13, pp. 31-41, Wiley Intersciences, John Wiley & Sons, 1988.

(Continued)

*Primary Examiner* — Nicholas Woodall

(57) ABSTRACT

A high pressure fluid jet system is provided, which is useful for cutting hard material during a surgical procedure. The cutting of hard material is more efficient as the system delivers abrasive solid particles with the high pressure fluid. A method of effecting cutting during a surgical procedure is also provided. In an exemplary embodiment, a surgical tool that is effective to deliver a pressurized stream of fluid through a nozzle is provided, and the pressurized stream of fluid is delivered through the surgical tool and out of the nozzle to hard material within a patient to effect cutting of the hard material within the patient in a desired pattern. The fluid that cuts the hard material can include a delivery liquid having a plurality of abrasive solid particles that are formed from an organic material. The abrasive solid particles can be entrained in the pressurized fluid stream or the pressurized fluid stream can erode a solid or suspension form of the abrasive particles.

7 Claims, 6 Drawing Sheets

U.S. PATENT DOCUMENTS

| | | | |
|---|---|---|---|
| 5,464,929 | A | 11/1995 | Bezwada et al. |
| 5,595,751 | A | 1/1997 | Bezwada et al. |
| 5,597,579 | A | 1/1997 | Bezwada et al. |
| 5,601,430 | A | 2/1997 | Kutsch et al. |
| 5,607,687 | A | 3/1997 | Bezwada et al. |
| 5,618,552 | A | 4/1997 | Bezwada et al. |
| 5,620,698 | A | 4/1997 | Bezwada et al. |
| 5,645,850 | A | 7/1997 | Bezwada et al. |
| 5,648,088 | A | 7/1997 | Bezwada et al. |
| 5,698,213 | A | 12/1997 | Jamiolkowski et al. |
| 5,700,583 | A | 12/1997 | Jamiolkowski et al. |
| 5,859,150 | A | 1/1999 | Jamiolkowski et al. |
| 6,126,513 | A | 10/2000 | Oshio et al. |
| 6,224,378 | B1 | 5/2001 | Valdes et al. |
| 6,325,624 | B1 | 12/2001 | Kutsch et al. |
| 6,726,693 | B2 | 4/2004 | Weber et al. |
| 7,063,713 | B1 | 6/2006 | Butsch et al. |
| 2002/0002030 | A1 | 1/2002 | Hertz |
| 2002/0058952 | A1 | 5/2002 | Weber et al. |
| 2003/0191449 | A1* | 10/2003 | Nash et al. ............ 604/523 |
| 2003/0207232 | A1 | 11/2003 | Todd et al. |
| 2004/0143269 | A1 | 7/2004 | Pude et al. |
| 2006/0100569 | A1 | 5/2006 | McRury et al. |
| 2006/0142773 | A1 | 6/2006 | Sengun et al. |

FOREIGN PATENT DOCUMENTS

| | | |
|---|---|---|
| JP | 1-121463 A | 5/1989 |
| JP | 2-015975 A | 1/1990 |
| JP | 09-276292 A | 10/1997 |
| JP | 2003-286356 A | 10/2003 |
| WO | 02/053014 A2 | 7/2002 |
| WO | 03/055397 A1 | 7/2003 |

OTHER PUBLICATIONS

Cohn and Younes, Journal of Biomaterials Research, vol. 22, pp. 993-1009, 1988.

Cohn, Polymer Preprints (ACS Division of Polymer Chemistry), vol. 30(1), p. 498, 1989 (e.g., PEO/PLA).

Heller, Handbook of Biodegradable Polymers, edited by Domb, et al., Hardwood Academic Press, pp. 99-118 (1997).

Kemnitzer and Kohn, Handbook of Biodegradable Polymers, edited by Domb, et. al., Hardwood Academic Press, pp. 251-272 (1997).

Vandorpe, et al., Handbook of Biodegradable Polymers, edited by Domb, et al., Hardwood Academic Press, pp. 161-182 (1997).

* cited by examiner

ABRASIVE CUTTING SYSTEM AND METHOD

CROSS REFERENCE TO RELATED APPLICATIONS

This application is a divisional of U.S. Patent Application Publication No. 2006/0142773 filed on Dec. 29, 2004, entitled "Abrasive Cutting System and Method," and now abandoned, which is hereby incorporated by reference in its entirety.

FIELD OF THE INVENTION

The present invention relates to high pressure fluid jet surgical tools, and in particular to a high pressure fluid jet tool for cutting hard material during a surgical procedure.

BACKGROUND OF THE INVENTION

Fluid pressure-based surgical tools for cutting bone and the like can offer some advantages over traditional surgical cutting devices and methodologies. In particular, high pressure fluid jets tend to emulsify the target material, thus avoiding thermal damage which can arise from using laser cutters and electrosurgical cutters. The emulsified material can also be easily transported away from the surgical site by aspiration. Indeed, the fact that many high pressure fluid jet cutting devices include aspiration and evacuation as an integral portion of the device can be an added benefit for many surgical procedures.

One drawback associated with current fluid pressure-based surgical systems which are used to cut bone and the like is that they typically require ultra-high operating pressures, and the delivery of such hydraulic pressure using a conservatively sized operating room pump and surgical instruments delicate enough to meet the surgeon's demands can often be problematic.

Accordingly, there remains a need for an improved fluid pressure-based surgical tool, and in particular a fluid pressure-based surgical tool for cutting hard material.

SUMMARY OF THE INVENTION

Various methods and devices are provided for cutting hard material, such as bone and the like, during a surgical procedure. In one exemplary embodiment, a method is provided which includes delivering a pressurized stream of fluid through a surgical tool to effect cutting of hard material within a patient. While a variety of fluids can be used to effect cutting, by way of non-limiting example, the fluid that cuts the hard material includes a delivery liquid having a plurality of abrasive solid particles formed from an organic material. The abrasive solid particles can be formed from a variety of materials, and in an exemplary embodiment they are formed from bioabsorbable materials such as polyglycolic acid, polylactic acid, polyethylene oxide, and blends and copolymers thereof.

The present invention also provides various methods for mixing the abrasive solid particles with the delivery liquid, such as, for example, mixing the abrasive solid particles with the pressurized stream of fluid prior to delivery through the nozzle. In another embodiment, the abrasive solid particles can be entrained in the pressurized fluid stream after the pressurized fluid stream exits the nozzle, or, alternatively, the abrasive solid particles be in the form of a solid or suspended material that is eroded by the pressurized fluid stream once the fluid stream exits the nozzle. While the solid material can be a variety of shapes, by way of non-limiting example, the solid material can be a rod. Moreover, the solid material can be a plate having a solid region and an open region. The open region of the plate can be a variety of configurations, and in one embodiment it can be formed in a variety of shapes and of a material such that when the plate is contacted by the pressurized fluid stream, the hard material is cut in a pattern that is complementary to the shape of the open region.

The present invention also provides a system for cutting tissue during a surgical procedure which includes a surgical apparatus effective to deliver a stream of pressurized fluid and a plate with a cutting template. The cutting template can have a variety of configurations, and in one embodiment, the cutting template can have a region formed of a solid material which is resistant to erosion by the pressurized fluid and an opening formed in said region which is able to be occluded by an erodable plug of abrasive material.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
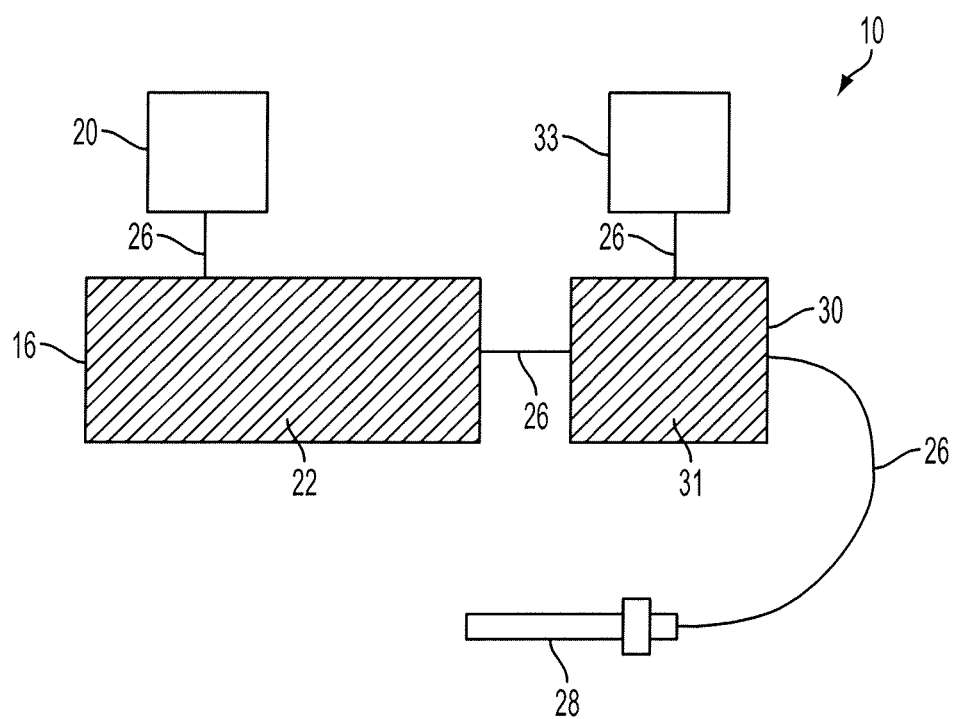
FIG. 1A is a schematic illustration of a high pressure fluid jet system according to one embodiment of the invention.

Certain exemplary embodiments will now be described to provide an overall understanding of the principles of the structure, function, manufacture, and use of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides a high pressure fluid jet system that is useful, during a surgical procedure, for cutting hard material. The cutting of hard material is more efficient as the system delivers abrasive solid particles with the high pressure fluid. In an exemplary embodiment, abrasive solid particles can be mixed with a pressurized stream of fluid prior to delivery of the fluid to a nozzle of an application tool. Alternatively, the abrasive solid particles can be entrained in the pressurized fluid stream or the pressurized fluid stream can erode a solid or suspension form of the abrasive particles. One skilled in the art will appreciate that the present invention can be used to cut a variety of hard materials, such as bone, cartilage, bone cement, bioadhesives, or any other hard material found or used within a human body, and therefore can be used in a wide range of surgical procedures.

A variety of materials can be used to form the abrasive particles of the present invention, including organic and inorganic materials. In an exemplary embodiment, the abrasive particles are biocompatible and bioabsorbable. One skilled in the art will appreciate that the materials can be crystalline or amorphous. Further, the crystalline materials can include ice and other frozen materials.

Examples of suitable bioasborbable materials that can be used to form the abrasive particles include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.), and any blends and copolymers thereof.

For the purpose of this invention aliphatic polyesters include, but are not limited to, homopolymers and copolymers of lactide (which includes lactic acid, D-,L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, $\alpha$, $\alpha$ diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly (ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, are understood to include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and ,-caprolactone are understood to be those as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al., Hardwood Academic Press, pp. 161-182 (1997). Polyanhydrides are understood to include those derived from diacids of the form HOOC—$C_6H_4$—O—$(CH_2)_m$—O—$C_6H_4$—COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are understood to be those as described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Finally, polyorthoesters are understood to be those as described by Heller in *Handbook of Biodegradable Polymers*, edited by Domb, et al., Hardwood Academic Press, pp. 99-118 (1997).

Exemplary bioabsorbable materials include, but are not limited to, polygylcolic acid, polylactic acid, and polyethylene oxide, and blends and copolymers thereof. Alternatively, inorganic materials can be used to form the abrasive particles, such as, for example, tricalcium phosphate.

The resulting abrasive particles can be any size which allows for effective cutting of the hard material, while at the same time does not deteriorate the nozzle of the high pressure fluid jet. In an one embodiment, the abrasive particles can have a size in the range of about 5 microns to 200 microns, depending upon when the abrasive particles are mixed with the pressurized stream of fluid. For example, if the abrasive particles are mixed with the high pressure jet prior to the high pressure jet flowing through the nozzle, the abrasive particles can be sized so as not to clog or diminish the performance of the nozzle. Thus, in an exemplary embodiment, the abrasive particles may be sized substantially smaller than the size of the nozzle, such as, for example, in the range of about 5 microns to 20 microns. Alternatively, for applications involving mixing the abrasive particles after the high pressure jet leaves the nozzle, where clogging or diminishing the performance of the nozzle is not as great of a concern, the particles can be a variety of sizes, such as, for example, in the range of about 5 microns to 200 microns.

While virtually any type of high pressure fluid jet system can be used with the various embodiments disclosed herein, the system generally includes a drive mechanism and a fluid source. While the fluid source can utilize a variety of fluids that can safely be delivered into the human body, in an exemplary embodiment, the fluid is saline. Further, the fluid can flow through the system at various rates depending upon the type of material desired to be cut, however the pressure of the stream of fluid is generally in the range of about 5 to 50,000 psi, more preferably in a range of about 1,000 to 20,000 psi, and most preferably in a range of about 5,000 to 15,000 psi. Following the combination of the abrasive materials and delivery liquid with the pressurized stream of fluid, the concentration of abrasive materials within the pressurized stream of fluid is generally no more than about 30% by volume, and more preferably in the range of about 5%-20% by volume.

FIG. 1A illustrates one exemplary embodiment of a high pressure fluid jet system 10 that is useful to cut hard materials in a surgical procedure by combining particles of an abrasive material with a stream of pressurized fluid. As shown, the system 10 can include a fluid source 20, such as a saline, that is in fluid communication with a drive mechanism 16. The drive mechanism 16 communicates the fluid to a suspension pump drive mechanism 31 such that a concentrated suspension of abrasive particles and delivery liquid, such as saline, (the "slurry") 33 can be combined with a pressurized stream of fluid prior to the pressurized stream of fluid entering a fluid jet delivery device or an application tool 28. The fluid source 20 can be coupled to the drive mechanism 16 using a variety of techniques, but in one exemplary embodiment the fluid source 20 includes a conduit 26 (discussed in more detail below) that extends between the fluid source 20 and the drive mechanism 16. Likewise, the drive mechanism 16, the suspension pump drive mechanism 31, and the application tool 28 can also be connected by a conduit 26 extending therebetween. A person skilled in the art will appreciate that the high pressure fluid jet system can include a variety of other components, and that each component can have a variety of configurations. Moreover, the components can be integrally formed with one another or they can be removably attached to one another.

While virtually any known drive mechanism 16 can be used, the drive mechanism 16 can include a pump console 22 for pumping fluid from the fluid source 20 through a pump cartridge (not shown) at a controlled rate. The exemplary pump console 22 can include a push rod that is driven by a motor disposed within the pump console 22, and that includes controls to allow a user to input the desired pump parameters. In use, the motor is effective to reciprocate the push rod along its axis, thereby reciprocating a piston disposed within the pump cartridge to pump fluid through the cartridge towards the application tool 28.

Figure 1B:
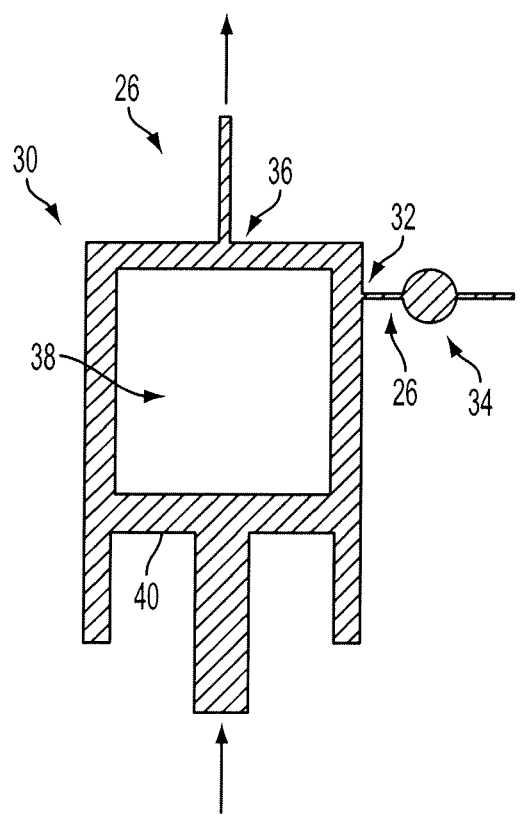
FIG. 1B is a schematic illustration of a suspension pump for use with the high pressure fluid jet system of FIG. 1A.

Connected to drive mechanism 16 (by conduit 26) is a suspension pump drive mechanism 31 which delivers a concentration of slurry 33 into the pressurized stream of fluid. The slurry can include any combination of the abrasive materials disclosed herein mixed or suspended within a delivery liquid, e.g., saline. However, by way of non-limiting example, the slurry contains at least about 40% of abrasive solid particles by volume, and in a preferred embodiment at least about 20% of abrasive solid particles by volume. The suspension pump drive mechanism 31 is similar to the drive mechanism 16 and, as shown in FIG. 1B, has a slurry pump console 30 which can include a piston 40 which slidably moves within a pump cavity 38 such that the slurry is pushed into the pressurized stream of fluid.

The pump cavity 38 of slurry pump console 30 can have a variety of configurations, however it generally is complementary in shape to the piston 40 and has an inlet port 32 through which the slurry enters the cavity 38 and an outlet 36 through which the slurry exits the cavity to ultimately mix with the pressurized stream of fluid. The inlet port 32 can be of any size, shape and configuration that renders it capable of transporting the slurry. In one embodiment, however, it is a conduit 26 (discussed in more detail below) reversibly or integrally mated to a valve mechanism 34. A variety of valve mechanisms 34 can be used so long as they are capable of controlling the rate and amount of slurry which enters into the cavity 38, such as, for example, a manual valve, a two-way valve, a one-way valve, or an automatically or electronically controlled valve. One skilled in the art will appreciate that the ability to control the amount of slurry entering the cavity 38, and ultimately the application tool 28, allows a surgeon to perform a variety of different procedures using a variety of different abrasive materials.

While the piston 40 can have any known configuration, the piston 40 is generally constructed so that it is able to move within the pump cavity 38 such that the slurry is dispensed through an outlet 36 towards the application tool. The outlet 36 can also be of any configuration known in the art to transport the slurry, however, by way of non-limiting example, it is an integrally formed or removably mated conduit 26 (such as is discussed below). Once the slurry is dispensed through the outlet 36, the piston 40 can then retract, thereby allowing slurry to refill the pump cavity 38.

Referring back to FIG. 1A, the fluid delivery conduit 26 can also have a variety of configurations. In one exemplary embodiment, the fluid delivery conduit 26 can be formed from a material which has sufficient burst strength to safely deliver fluid at a high pressure to the application tool 28. The material should also be flexible to enable a surgeon to manipulate the application tool 28 freely. The fluid delivery conduit 26 can also include connectors, which in an exemplary embodiment can be hand tightened, to connect the ends of the fluid delivery conduit 26 to the fluid source 20, drive mechanism 16, suspension pump drive mechanism 31, and/or application tool 28, where detachable components are desired. As previously indicated, the fluid delivery conduit 26 can be integrally formed with or removably mated to the fluid source 20, drive mechanism 16, suspension pump drive mechanism 31, and/or application tool 28.

The application tool 28 can also have a variety of configurations, and virtually any device for forming a high pressure fluid jet can be used with the various embodiments disclosed herein. For example, the application tool 28 can include a lumen in fluid communication with the delivery conduit 26 and a nozzle for forming a high pressure fluid jet. The application tool 28 can also include an evacuation lumen for collecting and withdrawing fluid, as well as a variety of other features for facilitating use of the device. By way of non-limiting example, one exemplary embodiment of a fluid jet device is disclosed in commonly owned U.S. patent application Ser. No. 10/904,456 filed on Nov. 11, 2004 and entitled "Methods and Devices for Selective Bulk Removal and Precision Sculpting of Tissue" by McRury et al.

Figure 2:
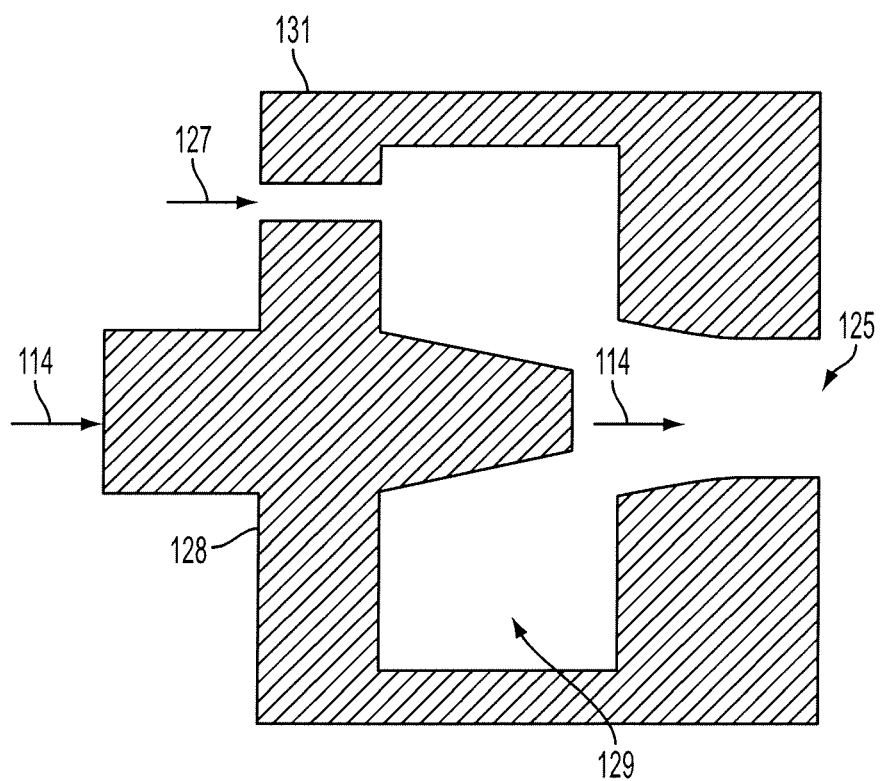
FIG. 2 is a schematic illustration of one embodiment of the present system utilizing a collimating nozzle which allows abrasive solid particles to be entrained within a pressurized stream of fluid.

FIG. 2 illustrates another embodiment of the present invention in which abrasive particles are entrained in a pressurized stream of fluid 114 after the fluid exits a nozzle 128 of an application tool or fluid jet delivery device. As shown, a second, collimating nozzle 131 surrounds the nozzle 128 of the application tool and forms a cavity 129 which maintains the slurry around the nozzle so that when the pressurized stream of fluid 114 enters the cavity 129, some of the abrasive particles in the slurry become entrained within it, and the abrasive-containing pressurized stream of fluid exits the cavity 129 through opening 125.

While the collimating nozzle 131 can have a variety of shapes, in one embodiment the collimating nozzle 131 has a shape which complements the shape of the nozzle 128 of the application tool. The collimating nozzle 131 can also have an inlet port 127 which allows for the entry of the slurry into the cavity 129, and in a preferred embodiment, the inlet port 127 includes a conduit (not shown) which is connected to a large supply of the concentrated slurry.

While the cavity 129 can be a variety of shapes, as shown, the cavity 129 is complementary to the shape of the collimating nozzle 131. The cavity 129 further can be a variety of sizes, however it should be large enough to maintain a presence of slurry around the nozzle 128 of the application tool. In use, once the cavity 129 is filled with slurry, the pressurized stream of fluid 114 flows into the cavity 129 via the nozzle 128. The influx of the pressurized stream of fluid 114 into the cavity 129 creates suction or a vacuum within the cavity 129, and, as a result, the slurry becomes entrained with the pressurized stream of fluid 114. The abrasive-containing pressurized fluid stream exits opening 125 in the collimating nozzle 131, and can then be used to cut hard material upon contact. One skilled in the art will appreciate that this embodiment provides the option of on-demand control to engage and/or disengage the flow of the abrasive material.

Figure 3:
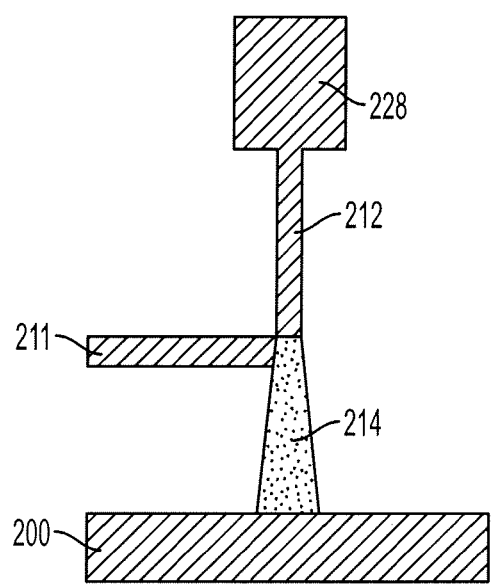
FIG. 3 is a schematic illustration of another embodiment of the present system utilizing a high pressure fluid jet system having a supply of abrasive solid particles.
Figure 4A:
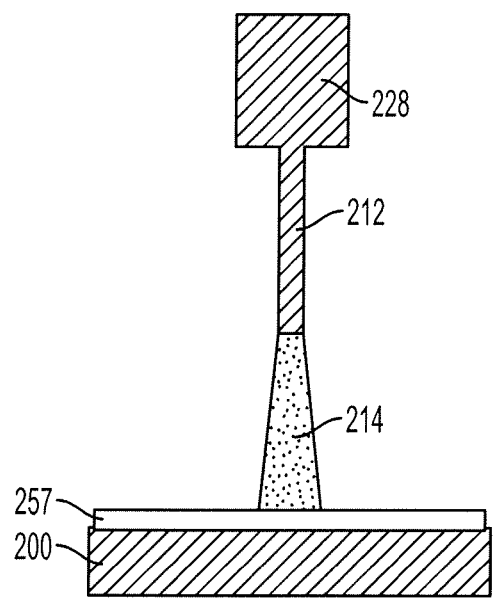
FIG. 4A is a schematic illustration of a further embodiment of the present system utilizing a high pressure fluid jet system for use with a cutting template that is eroded by a pressurized stream of fluid.
Figure 4B:
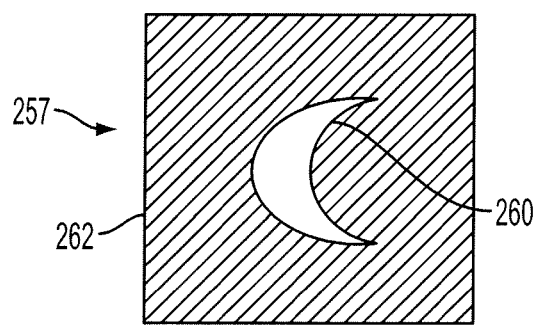
FIG. 4B is top perspective view of a cutting template for use with the high pressure fluid jet system of FIG. 4A.

FIGS. 3-4B illustrate alternative embodiments of the present invention in which the pressurized fluid stream can erode a suspension or solid form of the abrasive material resulting in the abrasive solid particles becoming entrained within the pressurized stream of fluid. Referring first to FIG. 3, the pressurized stream of fluid 214 flows out of the nozzle 228 of the high pressure jet 212 and contacts a supply 211 which contains the abrasive material. Once the pressurized stream of fluid contacts the supply 211, a portion of the abrasive material is eroded, resulting in abrasive particles becoming entrained within the pressurized stream of fluid 214 such that hard material 200 can be cut upon contact.

One skilled in the art will appreciate that the supply 211 of abrasive material can be a variety of forms, depending upon the type of material used. In exemplary embodiments, the supply 211 can be a solid which is rod-shaped (as shown), cylindrical, or any other shape, or a suspension. Further, the supply 211 can have any configuration which can hold the abrasive material, such as, for example, a conduit. The supply 211 can be directed to the pressurized fluid stream 214 in a variety of ways, however, in an exemplary embodiment it is cross-fed into the pressurized fluid stream 214. One skilled in the art will further appreciate that this embodiment requires a very short residence time of the abrasive before it is delivered to the hard material, so that abrasive materials other than those mentioned above, such as crushed ice, may be used.

FIGS. 4A-4B illustrate an alternative embodiment of the present invention in which the pressurized stream of fluid 214 erodes a portion of a cutting template 257 placed on the hard material 200. The cutting template 257 can be any form which allows for hard material to be cut in a desired pattern, however, by way of non-limiting example, the template 257 can have a solid region 262 and an open region 260, as shown in FIG. 4B. The solid region 262 can be made of any biocompatible material such as a metal (e.g., stainless steel) or a polymer (e.g., high density polyethylene or Polyetherether Ketone (PEEK)), or any other material that will not erode when contacted by the pressurized stream of fluid. The solid region 262 can also be a variety of shapes, such as a plate or, a cartridge, so long as the shape can contain within it an open region or cutting region (such as open region 260, for example) having an agglomerate of abrasive material. The open region 260 can be formed from any occlusion of the abrasive materials listed herein and can be a variety of shapes depending upon the type of cut desired by the surgeon, such as a line, a plug, a circle, etc., however as shown the open region 260 is a crescent shape.

In use, as shown in FIG. 4A, the pressurized stream of fluid 214 flows out of the nozzle 228 of the high pressure jet 212 and contacts the template 257. Upon contact, the abrasive material in the open region 260 is eroded by the pressurized stream of fluid 214, resulting in abrasive particles becoming entrained within the pressurized stream of fluid 214 while the solid region 262 remains unchanged. As a result, the hard material 200 is cut in a pattern which complements the pattern of the open region 260. One skilled in the art will appreciate that because the solid region 262 does not erode upon contact with the pressurized stream of fluid 214, it can be reused.

One skilled in the art will further appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of effecting cutting during a surgical procedure, comprising:
   providing a surgical tool effective to deliver a pressurized stream of a fluid through a nozzle;
   providing a cutting template having a region formed of a solid material resistant to erosion the pressurized fluid stream and an opening in said region forming a cutting region having a size and shape corresponding to a desired pattern. the cutting region being occupied by a plug of abrasive material; and
   directing the pressurized stream of fluid through the surgical tool, out of the nozzle, and over the cutting template to entrain with the pressurized fluid stream a plurality of abrasive solid particles formed from an organic material and eroded from the plug of abrasive material to effect cutting of hard material within a patient in a desired pattern.

2. The method of claim 1, wherein the delivery liquid is a saline solution.

3. The method of claim 1, wherein the abrasive solid particles are bioabsorbable.

4. The method of claim 1, wherein the abrasive solid particles are selected from the group consisting of polyglycolic acid, polylactic acid, polyethylene oxide, and blends and copolymers thereof.

5. The method of claim 4, wherein the abrasive solid particles are formed from particles having a particle size in the range of about 5 to 200 microns.

6. The method of claim 1, wherein the pressurized stream of fluid is delivered through the nozzle at a pressure in the range of about 1,000 to 20,000 psi.

7. The method of claim 1, wherein the hard material is selected from the group consisting of bone, bone cement, and bioadhesives.

* * * * *